(12) United States Patent
Leech et al.

(10) Patent No.: US 9,198,430 B2
(45) Date of Patent: Dec. 1, 2015

(54) ANTI-PARASITIC COMPOSITION COMPRISING A MACROCYCLIC LACTONE AND LEVAMISOLE AND METHOD OF TREATMENT OF PARASITIC INFESTATION

(75) Inventors: Wayne Frederick Leech, Auckland (NZ); Fadil Al Alawi, Auckland (NZ); Karthigeyan Nanjan, Hamilton (NZ)

(73) Assignee: BAYER NEW ZEALAND LIMITED, Hamilton (NZ)

( * ) Notice: Subject to any disclaimer, the term of this patent is extended or adjusted under 35 U.S.C. 154(b) by 87 days.

(21) Appl. No.: 14/129,101

(22) PCT Filed: Jun. 22, 2012

(86) PCT No.: PCT/NZ2012/000104
§ 371 (c)(1),
(2), (4) Date: Mar. 25, 2014

(87) PCT Pub. No.: WO2012/177151
PCT Pub. Date: Dec. 27, 2012

(65) Prior Publication Data
US 2014/0221299 A1    Aug. 7, 2014

(30) Foreign Application Priority Data
Jun. 23, 2011   (NZ) .......................... 593713

(51) Int. Cl.
| | | |
|---|---|---|
| A61K 31/70 | (2006.01) | |
| A01N 43/90 | (2006.01) | |
| A61K 31/429 | (2006.01) | |
| A61K 45/06 | (2006.01) | |
| A61K 31/7048 | (2006.01) | |
| A01N 57/16 | (2006.01) | |
| A61K 47/26 | (2006.01) | |
| A61K 9/00 | (2006.01) | |

(52) U.S. Cl.
CPC ............... *A01N 43/90* (2013.01); *A01N 57/16* (2013.01); *A61K 9/0019* (2013.01); *A61K 31/429* (2013.01); *A61K 31/7048* (2013.01); *A61K 45/06* (2013.01); *A61K 47/26* (2013.01)

(58) Field of Classification Search
CPC ..... A01N 43/90; A01N 57/16; A61K 31/429; A61K 45/06; A61K 31/7048
See application file for complete search history.

(56) References Cited

U.S. PATENT DOCUMENTS

| | | | | |
|---|---|---|---|---|
| 5,773,422 | A | * | 6/1998 | Komer ............................ 514/30 |
| 2006/0128641 | A1 | * | 6/2006 | Holmes et al. .................. 514/28 |
| 2011/0144046 | A1 | | 6/2011 | Hillier |

FOREIGN PATENT DOCUMENTS

| | | |
|---|---|---|
| CN | 1375293 A | 10/2002 |
| NZ | 508969 A | 12/2001 |
| NZ | 552293 A | 3/2009 |
| NZ | 584629 A | 12/2010 |
| NZ | 570591 A | 1/2012 |
| WO | 0074489 A1 | 12/2000 |
| WO | 2004009080 A1 | 1/2004 |
| WO | 2004069242 A1 | 8/2004 |
| WO | 2007068073 A2 | 12/2006 |
| WO | 2008072985 A2 | 6/2008 |
| WO | 2008075984 A3 | 6/2008 |
| WO | 2010021555 A1 | 2/2010 |
| WO | 2011143479 A1 | 11/2011 |

OTHER PUBLICATIONS

Heitzman, Dr. Raymond J., "Residues in Food and Their Evaluation," Addendum to the Doramectin Residue Monograph by the 45th Meeting of the Committee and published in FAO Food and Nutrition Paper 41/8, Rome 1996.

* cited by examiner

*Primary Examiner* — Elli Peselev
(74) *Attorney, Agent, or Firm* — Jonathan R. Harris; Yonggang Ji

(57) ABSTRACT

This invention relates to a veterinary antiparasitic solubilized composition including a macrocyclic lactone or a pharmaceutically equivalent salt thereof, and levamisole or a pharmaceutically equivalent salt thereof, characterized in that the pH of the composition is in the range of 2.0 to 5.0 and wherein the composition includes at least one surfactant and at least one antioxidant.

17 Claims, No Drawings

ANTI-PARASITIC COMPOSITION COMPRISING A MACROCYCLIC LACTONE AND LEVAMISOLE AND METHOD OF TREATMENT OF PARASITIC INFESTATION

TECHNICAL FIELD

This invention relates to an anti-parasitic composition.

BACKGROUND ART

In preferred embodiments of the present invention, this invention relates to a composition for the use in the treatment of non-human animals, such as domesticated and farm animals.

There is a considerable loss of productivity worldwide due to the effect of parasites on farm animals. Such parasites can include gastrointestinal round worms, lung worms, eye worms, parasitic stage grubs, biting and sucking lice, ticks, mites, screw worm and horn flies.

As a consequence, a considerable amount of money, time and effort has been spent in developing compositions to treat animals for these parasites.

Typically, treatment compositions are based upon having a broad spectrum macrocyclic lactone as the primary active ingredient.

However, with the wide spread usage of the macrocyclic lactones, resistance has built up in the parasites and treatment compositions are becoming less effective.

Increasing the dosage level is not a ready solution. Firstly, an increased dosage could cause significant side effects and may affect the health of the animal.

The main concern, however, is that increased dosages lead to residual drug concentrations in the animal being higher. This causes a longer withhold time on the treated animals before they can be slaughtered for human consumption. The flow on effect of the animals not being timely slaughtered increases herd management costs and subsequently consumer cost.

It should be therefore appreciated that there could be provided a composition and method of treatment that addresses the issues of combating resistance amongst parasites as well as minimal side effects and withhold times.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DISCLOSURE OF THE INVENTION

According to one aspect of the present invention there is provided a veterinary anti-parasitic solubilised composition including
 a macrocyclic lactone or a pharmaceutically equivalent salt thereof, and
 levamisole or a pharmaceutically equivalent salt thereof, characterised in that the pH of the composition is the range of 2.0 to 5.0 and wherein the composition includes at least one surfactant and at least one antioxidant.

According to another aspect of the present invention there is provided a method of treating non-human animals for parasitic infestation, the composition including a macrocyclic lactone or a pharmaceutically equivalent salt thereof, and levamisole or a pharmaceutically equivalent salt thereof, wherein the pH of the composition is in the range of 2.0 to 5.0 and wherein the composition includes at least one surfactant and at least one antioxidant
characterised by the step of administering a veterinary anti-parasitic solubilised composition to a non-human animal in need thereof.

Preferred macrocyclic lactones are selected from the avermectin and milbemycin derivatives, including but not limited to abamectin, doramectin, eprinomectin, ivermectin, moxidectin, and milbemectin.

A particularly preferred macrocyclic lactone is doramectin, which is well recognised as being useful as an antiparasitic agent. A popular product which incorporates doramectin is Dectomax™, which is widely used on New Zealand cattle.

However, like many other macrocyclic lactones, doramectin is only fully effective against a proportion of parasites as a result of increasing resistance being built up. Despite this, there is still less resistance with doramectin than other products (such as ivermectin), and it is comparatively cost effective (compared to, for example Moxidectin).

Levamisole was chosen as the other active to be used in the composition because the inventors recognised that it would provide a synergistic effect by being effective against those parasites resistant to doramectin.

The combination of doramectin and levamisole is not one that has to the inventors' knowledge been contemplated because these two actives are thought to be incompatible with each other due to quite different pH ranges being preferred.

In preferred embodiments, the present invention is provided in the form of an injectable composition. However this can be administered via other methods such as orally or as a pour on.

A discussion of the trial results follows, but in summary significant and unexpected advantages were found by using the present invention in cattle, when compared against the use of the incumbent Dectomax™ formulation and untreated animals.

The applicants experience in the veterinary industry leads it to believe that the present invention will also be effective when applied to other farm species such as sheep. For example, they expect lower injection site residues as per cattle and better efficacy as resistance to doramectin in sheep becomes more common.

These results included a significant improvement in efficacy when doramectin resistance was found to be present. In particular, the present invention was highly effective against such resistant *Cooperia* and *Trichostrongylus* when compared to Dectomax™.

Another significant advantage found by the use of the present invention is that residues, specifically at the injection site, were found not to persist for as long and at the high levels found for a standard doramectin product.

In preferred embodiments of the present invention, the effective amount of macrocyclic lactone within the composition is in the order of 0.2 to 1.2% w/v. This compares with the effective amount of macrocyclic lactone (doramectin) in Dectomax™ which is in the order of 1% w/v.

In preferred embodiments of the present invention, the effective amount of levamisole in composition is the range of 6 to 27% w/v. This has been confirmed by the applicants to be an effective amount in terms of killing off parasites but also maintaining animal health and co-existing with doramectin in a stable solution.

It is envisaged that levamisole may be provided in the form of levamisole hydrochloride or levamisole phosphate. Levamisole phosphate is preferred as there are less irritation issues at site of injection than levamisole hydrochloride. In the composition it is preferred to be in the range of 10 to 40% w/v.

One of the difficulties of formulating with levamisole is that it prefers a pH of around about 3, whereas other actives tend to be stable in solution with a more neutral pH.

In preferred embodiment of the present invention, the pH range of the composition is in the order of 2.0 to 5.0.

More preferably the pH range of the composition is in the order of 3.0 to 4.5.

As will be seen in subsequent trial data, the careful choice of preferred excipients and concentrations was required to help maintain both the macrocyclic lactone and levamisole in solution and with an appropriate pH.

In preferred embodiments of the present invention, one of the excipients is a chelating agent to chelate any heavy metals which would facilitate the oxidation of actives. A preferred chelating agent is EDTA disodium, although other agents can be used. Other salts of EDTA may be used as well including sodium, calcium and potassium. Further chelating agents that may be used include citric acid monohydrate, fumaric and malic acid.

In preferred embodiments, the composition also includes an antioxidant. This is a preferred inclusion in the composition because it stabilise the actives in the product from oxidation. In particular, the inventors found the incorporation of an antioxidant to be beneficial in preventing degradation of the macrocyclic lactone, which may otherwise be unstable at the preferred low pH of the composition.

Suitable antioxidants include BHA, vitamin E, propyl gallate, TBHQ, sodium metabisulphate.

A preferred antioxidant is butylated hydroxytoluene (BHT) because BHT is the usual stabilizer for mectins.

Preferably, the antioxidant is present in the composition at or above 0.15% w/v.

More preferably, the antioxidant is present in the composition at or above 0.20% w/v.

Most preferably, the antioxidant is present in the composition at approximately 0.25% w/v.

Surprisingly the inventors found that the conventional amount of antioxidant (0.1 to 0.15% w/v) used in injectable compositions may not be sufficient to stabilise the actives, and in particular the macrocyclic lactone. However, when the level of antioxidant was increased beyond conventional amounts, the stability may be significantly improved, which was difficult to achieve at this lower pH. It is thought that in combination with other excipients, such as stabilisers and/or surfactant, this stability may be synergistically improved.

Preferably, the composition also includes preservatives. Suitable preservatives include parabenz, thiomersals, cresols and chlorbutanol.

The preferred preservative is benzyl alcohol because it acts as a solubiliser and preservative at the same time.

Preferably, the composition also includes a stabiliser. Suitable stabilisers include polyols with preferred stabiliser being stabilised glycerine formal because it is already in a stabilised form.

In preferred embodiments, the composition also includes a surfactant which in the present invention assists in stabilising the macrocyclic lactone (e.g. doramectin) from the low pH of the product. It should be noted that the lower pH is required to stabilize the levamisole.

Preferably, the amount of surfactant in the composition is above 15% w/v.

More preferably, the amount of surfactant in the composition is approximately 20% w/v.

This is different to many past compositions, particularly those which strived, albeit unsuccessfully, to achieve a stable solubilised composition at a low pH below 4.0 (for example NZ 508969). The inventors found that increasing the level of surfactant helped to stabilise the macrocyclic lactone, in particular, from crystallisation at a pH between 2.0 to 5.0.

Again, the inventors saw that the stability may be synergistically improved when the surfactant is included together with the stabiliser and/or antioxidant.

Suitable surfactants include polysorbate 20, cremophor and peg-12 oleate. The preferred surfactant is Polysorbate 80, it is soluble in water and widely used in injectables.

Aspects of the present invention will now be described by way of example only with reference to various experiments and trials conducted by the applicant.

BEST MODES FOR CARRYING OUT THE INVENTION

As alluded previously in the patent specification, it can be very difficult to formulate a stable composition containing an effective amount of macrocyclic lactone (such as doramectin) and levamisole.

With regard to the present invention, it should be appreciated that the inventors are highly experienced formulation chemists particularly in the field of veterinary medicine. It is therefore significant that it took over forty attempts at formulating the present invention before a formulation was found that was storage stable and did not have crystal formulation at key temperatures.

Table 1 below is a summary of some of the trialled formulations.

TABLE 1

Trialled Formulations

| no | Ingredients | PF-1 % w/v | PF-2 % w/v | PF-3 % w/v | PF-4 % w/v | PF-5 % w/v | PF-6 % w/v | PF-7 % w/v | PF-8 % w/v | PF-9 % w/v | PF-10 % w/v | PF-11 % w/v | PF-12 % w/v | PF-13 % w/v |
|---|---|---|---|---|---|---|---|---|---|---|---|---|---|---|
| 1 | Doramectin** | 0.42 | 0.525 | 0.42 | 0.525 | 0.42 | 0.525 | 0.525 | 0.525 | 0.525 | 0.63 | 0.84 | 0.525 | 0.525 |
| 2 | Levamisole Hydrochloride** | 15.8 | 21 | 15.8 | 21 | 15.8 | 21 | 21 | 21 | 21 | 31.5 | 42 | 0 | 0 |

TABLE 1-continued

Trialled Formulations

| no | Ingredients | PF-1 % w/v | PF-2 % w/v | PF-3 % w/v | PF-4 % w/v | PF-5 % w/v | PF-6 % w/v | PF-7 % w/v | PF-8 % w/v | PF-9 % w/v | PF-10 % w/v | PF-11 % w/v | PF-12 % w/v | PF-13 % w/v |
|---|---|---|---|---|---|---|---|---|---|---|---|---|---|---|
| 3 | Levamisole Phosphate** | 0 | 0 | 0 | 0 | 0 | 0 | 0 | 0 | 0 | 0 | 0 | 26.25 | 26.25 |
| 4 | Disodium edetate | 0 | 0 | 0.1 | 0.1 | 0.1 | 0.1 | 0.1 | 0.1 | 0.1 | 0.1 | 0.1 | 0.1 | 0.1 |
| 5 | Butylated hydroxyl toluene | 0.25 | 0.05 | 0.25 | 0.25 | 0.25 | 0.25 | 0.25 | 0.25 | 0.25 | 0.25 | 0.25 | 0.25 | 0.25 |
| 6 | Benzyl alcohol | 0 | 0 | 2.5 | 2.5 | 2 | 2.5 | 3 | 3 | 3 | 4 | 4 | 3 | 3 |
| 7 | Glycerine formal stabilised | 40 | 40 | 0 | 0 | 0 | 0 | 0 | 0 | 20 | 0 | 0 | 0 | 20 |
| 8 | Propylene glycol | qs | qs | 0 | 0 | 0 | 0 | 0 | 20 | 0 | 20 | 20 | 20 | 0 |
| 9 | Polysorbate 80 | 0 | 0 | 8 | 8 | 10 | 12 | 20 | 20 | 20 | 20 | 20 | 20 | 20 |
| 10 | Citric acid | 0 | 0 | 2 | 2 | 2 | 2 | 2.2 | 2.2 | 2.2 | 2.2 | 2.2 | 2.2 | 2.2 |
| 11 | Sodium hydroxide | 0 | 0 | 0.6 | 0.6 | 0.6 | 0.6 | 0.6 | 0.5 | 0.5 | 0.4 | 0.4 | 0.3 | 0.3 |
| 12 | Water for injection | 0 | 0 | qs | qs | qs | qs | qs | qs | qs | qs | qs | qs | qs |

**5% overages added
PF-01 - solvent based - stability issue - not stable
PF-02 - solvent based - stability issue - not stable
PF-03 - water based - stability issue - not stable
PF-04 - water based - stability issue - not stable
PF-05 - water based - stability issue - not stable
PF-06 - water based - stability issue - not stable
PF-07, 08 & 09 - water based - crystal formation at 4° C.
PF-11- water based - changed to levamisole phosphate - due to the irritation of levamisole hydrochloride
PF-12 - water based - crystal formation at 4 & 40° C.

Different excipients, concentrations of actives and the buffer system were varied to determine how the stability of the macrocyclic lactone and levamisole actives were affected.

Surprisingly it was found that it is possible to prevent or significantly decrease degradation of a macrocyclic lactone an aqueous composition at low pH. This permits the use of a pH suitable for stabilising the levamisole component dissolved in the aqueous composition. This approach is preferred over a compromise that would require a pH in-between the low value suitable for levamisole and a neutral pH suitable for a macrocyclic lactone.

Even more surprisingly, it was found that the combination of macrocyclic lactone and levamisole could be stabilised in a composition containing the relatively high concentrations of actives that would generally be required for an injectable. The development of a composition suitable for injection can be complicated by the desire to increase the concentration of actives as compared to other types of compositions, to limit or reduce the volume of the composition that needs to be injected.

The macrocyclic lactone is solubilised using solvent that is fully soluble within the composition. Accordingly a true solution or micellar solution is formed rather than an emulsion. A preferred solvent is benzyl alcohol, which is an effective solvent for macrocyclic lactones, and also functions as a preservative. The solubility of the solvent within the composition can be increased with the use of co-solvents, such as the water miscible solvents glycerine formal and propylene glycol, which can also function as stabilisers. A skilled person would readily recognise other solvents systems that would also be suitable.

Using surfactant to enhance the solubility and/or stability of the actives is particularly preferred. The formation of a micellar solution is a preferred method of solubilising the macrocyclic lactone within the aqueous composition.

Table 2 below represents a preferred formulation in accordance with the present invention. This formulation has doramectin and levamisole in quantities that were shown to be highly effective against parasites. The formulation is stable without crystal formation and has minimal, if any, side effects on the animals.

TABLE 2

Preferred Formulation DL Injection

| Ingredient name | CAS number | Quantity (g/L) | Function |
|---|---|---|---|
| Doramectin | 117704-25-3 | 4.2* | Active ingredient |
| Levamisole phosphate | 32093-35-9 | 210* | Active ingredient |
| EDTA disodium | 139-33-3 | 1 | Chelating agent |
| Butylated hydroxytoluene (BHT) | 128-37-0 | 2.5 | Antioxidant |
| Benzyl alcohol | 100-51-6 | 35 | Preservative |
| Glycerine formal stabilised | 4740-78-7 5464-28-8 | 200 | Stabiliser |
| Polysorbate 80 | 9005-65-6 | 200 | Surfactant |
| Citric acid | 77-92-9 | 22 | pH adjuster |
| Sodium hydroxide | 1310-73-2 | 3 | pH adjuster |
| Water for injection | 7732-18-5 | q.s. | Solvent/vehicle |

*5% overage added

The pH of the composition was adjusted to around 3.9 using the citrate buffer system.

In particular, it was noted that to achieve stability and to keep the formulation in solution, a high percentage of surfactant was required. Without the presence of a surfactant in sufficient quantity, crystallisation and colour changes in the solution were observed.

Manufacturing Method

A preferred method of manufacturing the preferred embodiment comprises the steps of:

Step 1:
a. In a clean and dry manufacturing vessel load 30% of water for injection
b. Add and dissolve EDTA disodium with stirring
c. Add and dissolve citric acid with stirring
d. Add and dissolve sodium hydroxide with stirring
e. Add and mix glycerine formal stabilized
f. Add and dissolve levamisole phosphate with stirring
g. Check the clarity of the solution Step 2:

h. In a separate clean and dry manufacturing vessel load benzyl alcohol and heat to 50-55° C.
i. Add and dissolve BHT with stirring
j. Add and dissolve doramectin with stirring
k. Add warm Polysorbate 80 and mix well
l. Check the clarity of the solution Step 3:

m. Add 'Step 2' to 'Step 1' and mix well
n. Rinse the vessel from Step 2 with some water for injection and add the rinsate to the main bulk
o. Make up the final volume with water for injection and stir well
p. Check the pH—it should be 3.6-4.2

A considerable number of trials were conducted using a formulation in accordance with the present invention and comparing its effects against Dectomax™ and a control untreated group.

Table 3 below shows the mean faecal egg counts found in non-slaughtered cattle following treatment with the present invention (DL injection) and Dectomax™. This is from a sample size of 36 cattle.

As can be clearly seen, the egg counts 35 days after treatment for the present invention are still zero, whereas the Dectomax™ treated and the untreated cattle have significant faecal egg counts. This suggested resistance may be present in this trial.

TABLE 3

Mean Faecal Egg Counts in the non-slaughtered cattle following treatment with DL Injection and Dectomax

| Product applied | Days after treatment | | | | | | | |
|---|---|---|---|---|---|---|---|---|
| | −3 | 7 | 14 | 21 | 28 | 35 | 42 | 49 |
| DL injection | 121.4 | 0 (100) | 0 (100) | 0 (100) | 0 (100) | 0 (100) | 50.0 (73.1) | 50.0 (70.8) |
| Dectomax | 128.6 | 57.1 (71.5) | 21.4 (85.7) | 28.6 (80.0) | 57.1 (63.7) | 107.1 (40.0) | 135.7 (26.9) | 128.6 (25) |
| Untreated | 128.6 | 200.0 | 150.0 | 142.9 | 157.1 | 178.6 | 185.7 | 171.4 |

Table 4 below shows the mean faecal egg counts in slaughtered cattle of the same trial. Again, it indicates that the present invention may have significantly improved results when doramectin resistance is present compared to the industry's standard of Dectomax™.

TABLE 4

Mean Faecal Egg Counts in the slaughtered cattle following treatment with DL Injection, Dectomax or untreated

| Product applied | Days after treatment | | |
|---|---|---|---|
| | −3 | 7 | 13/14 |
| DL Injection | 288 | 0 (100) | 0 (100) |
| Dectomax | 250 | 22.2 (90.5) | 77.8 (67.0) |
| Untreated | 271.4 | 233.3 | 235.7 |

Likewise, Table 5 shows significant differences between the effect of the present invention on larval cultures compared with Dectomax™.

TABLE 5

Quantitative larval culture data for 50 g samples collected at varying times after treatment with DL injection, Dectomax or untreated in the non-slaughtered cattle

| Product applied | Days after Treatment | | | | | | |
|---|---|---|---|---|---|---|---|
| | −3 | 7 | 15 | 21 | 28 | 35 | 42 |
| DL injection | 22000 | 0 (100) | 15 (99.7) | 0 (100) | 8 (99.8) | 0 (100) | 6500 (19.8) |
| Dectomax | 22000 | 7600 (19.1) | 490 (90.9) | 410 (94.6) | 2300 (53.1) | 1100 (64.5) | 3100 (61.7) |
| Untreated | 22000 | 9400 | 5400 | 7600 | 4900 | 3100 | 8100 |

Number in brackets refers to the % control compared with the untreated group.

The interpretation of these results along with more detailed data (not provided in the specification) is given below.

The quantitative measuring of larval numbers can provide a more sensitive measure of the efficacy of the test products than egg counts, and the results in the non-slaughtered cattle indicated that DL injection appeared to effectively suppress the excretion of viable eggs for a period of at least 35 days.

Significantly, the level of control indicated by this single ingredient doramectin product was relatively low throughout the study, most likely because of resistant *Trichostrongylus* and *Cooperia*.

The quantitative larval culture results, also provided information about the species make up of the eggs being excreted. In both the slaughter and non-slaughter parts of the study, *Cooperia* were the dominant species of larvae found in the group treated with Dectomax 7, 13/14, 15, 21 and 28 days after treatment. In addition, significant numbers of *Trichostrongylus* larvae were found in the cattle treated with Dectomax at each of the post treatment samplings. Interestingly, this trend is consistent with the pattern found in the total worm count results.

As mentioned previously, the present invention appeared to be particularly effective in targeting doramectin resistant species and this was confirmed by the total worm count as can be seen in Table 6.

TABLE 6

Efficacy (%)[1] of the test and reference products against, *Trichostrongylus* spp. and *Cooperia* spp. based on total worm counts

| | Parasite species and life stage | | |
|---|---|---|---|
| Product | *Trichostrongylus axei* | Small intestinal *Trichostrongylus* spp. | *Cooperia* spp. |
| DL Injection | >99.9 | >99.9 | >99.9 |
| Dectomax | 79.3 | 83.8 | 97.6 |

[1]based on geometric means

The presence of doramectin resistant species in this trial is unequivocally confirmed for abomasal and small intestinal Trichostrongylus spp. when the individual total worm counts collected at slaughter for Dectomax is compared with the present invention (DL injection), see Table 7 below. The results, from the individual worm counts and % reduction in arithmetic means, against *Cooperia* are also very suggestive of emerging resistance to doramectin by this species. It can also be noted *Cooperia* spp. resistance to macrocyclic lactones has been documented in cattle in New Zealand.

TABLE 7

DL Injection

| Tag No | *Trichostrongylus axei* 5th Stage | Small intestinal *Trichostrongylus* spp. 5 th | *Cooperia* spp. 5 th |
|---|---|---|---|
| 48 | — | — | — |
| 57 | — | — | — |
| 239 | — | — | — |
| 242 | 50 | — | — |
| 309 | — | — | — |
| 438 | — | — | — |
| PVS080 | — | — | — |
| R74 | — | — | — |
| AM | 6.3 | 0.0 | 0.0 |
| GM | 0.6 | 0.0 | 0.0 |
| % Red AM | >99.9 | >99.9 | >99.9 |
| % Red GM | >99.9 | >99.9 | >99.9 |

Dectomax

| | | | |
|---|---|---|---|
| 59 | 450 | 200 | 450 |
| 236 | 600 | — | 400 |
| 237 | 500 | 250 | 8600 |
| 560 | 11000 | 100 | — |
| 573 | 15500 | 450 | — |
| 1039 | 850 | 350 | 2750 |
| 2066 | 6250 | 200 | — |
| 65 | 300 | 100 | 5150 |
| 233 | 3750 | — | 250 |
| AM | 4356 | 183.3 | 1956 |
| GM | 1728 | 63.1 | 120.8 |
| % Red AM | 71.9 | 76.5 | 83.8 |
| % Red GM | 79.3 | 83.8 | 97.6 |

AM = arithmetic mean,
GM = geometric mean

In particular, the results can be summarised as below:
1. DL Injection provided >99.9% control based on geometric means of *Ostertagia* spp, *Trichostrongylus axei*, small intestinal *Trichostrongylus* spp, *Cooperia* spp, *Oesophagostomum* spp, *Chabertia* sp and *Trichuris* spp.
2. Dectomax™ and DL Injection provided comparable levels of control of *Ostertagia* spp, *Oesophagostomum* spp, *Chabertia* sp and *Trichuris* spp.
3. Dectomax™ provided low levels efficacy of *T. axei* and small intestinal *Trichostrongylus* spp that were significantly different to those provided by DL Injection It can clearly be seen that the present invention is highly effective in its own right, but also in comparison with the current product where resistance to Doramectin is present.

Use of the present invention also has the added advantage of having much lower doramectin residues than a standard doramectin product particularly at the injection site. The JECFA (1996) Doramectin Monograph, in 'Residues of Some Veterinary Drugs in Animals and Foods, FAO Food and Nutrition Paper', No 41/8, pp 85-98 noted high concentrations of doramectin at the injection site during the 35 day period after parental administration of the unlabelled dose of a doramectin injection at the recommended label rate. The carrier used in this injection composition comprised 75% sesame oil and 25% ethyl oleate.

Within that report, table 8, shown below for day 21, 28 and 35, had mean doramectin residues at the injection site of 1900, 380 and 930 ug/kg after 21, 28 and 35 days respectively after treatment of unlabelled doramectin at 0.2 mg/kg bodyweight.

TABLE 8

Residues of Doramectin (ug/kg) in tissues of cattle after treatment with unlabelled doramectin at 0.2 mg/kg bodyweight.

| Tissue | Day 21 | Day 28 | Day 35 |
|---|---|---|---|
| Muscle | <7 | <4 | <3 |
| Liver | 107 | 66 | 29 |
| Kidney | 11 | 8.8 | <4.5 |
| Fat | 182 | 94 | 57 |
| Injection | 1900 | 380 | 930 |

In comparison to that treatment of cattle with our DL Injection had average doramectin residues in the injection site of 6.1, 13.7 and 2.8 ug/kg. Our tissue levels were also lower as shown in Table 9 below.

TABLE 9

Average doramectin residues (ug/kg) in various tissues of cattle treated with DL injection at 0.25 mg/kg b.w. doramectin

| Tissue site | Day 21 | Day 28 | Day 35 |
|---|---|---|---|
| Muscle | 2.5 | 2.5 | 2.5 |
| Liver | 15 | 2.5 | 2.5 |
| Kidney | 4.8 | 2.5 | 2.5 |
| Peri-renal fat | 19.1 | 2.5 | 2.5 |
| Subcutaneous fat | 28.0 | 2.5 | 2.5 |
| Injection site | 6.1 | 13.7 | 2.8 |

A preferred dosage regime that provided all of the previous results is provided in Table 10 below.

TABLE 10

Doramectin + Levamisole Injection Label Dosage Instructions

| Weight (kg) | Vol (mL) |
|---|---|
| 61-70 | 3.5 |
| 71-80 | 4.0 |
| 81-100 | 5.0 |
| 101-120 | 6.0 |
| 121-140 | 7.0 |
| 141-160 | 8.0 |
| 161-180 | 9.0 |
| 181-220 | 11.0 |
| 221-260 | 13.0 |
| 261-300 | 15.0 |

The dose rate for DL injection for cattle greater than 300 kg will be 1 mL/20 kg (0.2 mg/kg doramectin and 10 mg/kg levamisole phosphate).

Table 11 is the Dectomax™ label dosage instructions.

TABLE 11

Dectomax label dosage Instructions

| Liveweight | Dose Volume (mL) |
|---|---|
| 40-50 | 1 |
| 51-75 | 1.5 |
| 75-100 | 2.0 |
| 101-150 | 3.0 |
| 151-200 | 4.0 |
| 201-250 | 5.0 |
| 251-300 | 6.0 |
| 301-350 | 7.0 |
| 351-400 | 8.0 |

Cattle heavier than 400 kg are to be dosed at the rate of 1 mL/50 kg.

Site Reactions to DL Injections

A safety study was performed to evaluate the safety of the preferred formulation of the invention. The study was performed on four groups of cattle when dosed subcutaneously at 1× with a single dose and with a split dose, and 2× the maximum label dose rate, and intramuscularly at 1× the maximum label dose rate.

Injection site swellings were seen in most of the groups for the first four days following treatment. The resolution of the swelling at the injection sites was almost complete at seven days for the animals in the intramuscular injection group, but continued to resolve over the next 14 days following treatment for animals in the other groups.

It was noted that a large proportion of the swellings were only detected because the site of injection was carefully examined as part of the requirements of the study. However, under normal farm conditions where the site of injection is not viewed closely it was observed by the Investigator and the farmer that the majority of the site reactions that occurred in the current study would not have been noticed. It was concluded that administration of the DL injection, as recommended, was not associated with undue pain, inflammation, or distress.

Aspects of the present invention have been described by way of example only and it should be appreciated that modifications and additions may be made thereto without departing from the scope thereof as defined in the appended claims.

What we claim is:

1. A veterinary antiparasitic solubilised injectable composition comprising
   a macrocyclic lactone or a pharmaceutically equivalent salt thereof, and
   a levamisole salt,
   wherein the pH of the composition is in the range of 2.0 to 5.0 and wherein the composition includes at least 15% w/v surfactant.

2. A composition as claimed in claim 1 wherein the effective amount of levamisole in the composition is in the range of 6.0% to 27.0% w/v.

3. A composition as claimed in claim 1 wherein the levamisole is provided in the form of levamisole hydrochloride.

4. A composition as claimed in claim 1 wherein the levamisole is provided in the form of levamisole phosphate.

5. A composition as claimed in claim 1 wherein the macrocyclic lactone is in the range of 0.2 to 1.2% w/v.

6. A composition as claimed in claim 1 further comprising a chelating agent.

7. A composition as claimed in claim 6 wherein the chelating agent is EDTA disodium.

8. A composition as claimed in claim 1 further comprising an antioxidant.

9. A composition as claimed in claim 8 wherein the antioxidant is butylated hydroxytoluene.

10. A composition as claimed in claim 1 further comprising a preservative.

11. A composition as claimed in claim 10 wherein the preservative is benzyl alcohol.

12. A composition as claimed in claim 1 further comprising a stabiliser.

13. A composition as claimed in claim 12 wherein the stabiliser is glycerine formal.

14. A composition as claimed in claim 1 wherein the concentration of surfactant in the composition is approximately 20% w/v.

15. A composition as claimed in claim 1 wherein the surfactant is Polysorbate 80.

16. A method of treating a non-human animal for parasitic infestation comprising the step of
   administering to the animal the veterinary composition as claimed in claim 1 by injection.

17. A composition as claimed in claim 8 wherein the concentration of antioxidant in the composition is above 0.15% w/v.

* * * * *